United States Patent [19]
Brown

[11] Patent Number: 6,109,109
[45] Date of Patent: *Aug. 29, 2000

[54] HIGH ENERGY, LOW FREQUENCY, ULTRASONIC TRANSDUCER

[75] Inventor: Albert E. Brown, Hayward, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/175,096

[22] Filed: Oct. 19, 1998

[51] Int. Cl.⁷ .................................................. G01N 29/00
[52] U.S. Cl. ............................................. 73/632; 367/159
[58] Field of Search ............................... 73/632; 310/311, 310/321, 322, 323, 325, 326, 327, 329, 331, 332, 330, 334, 367, 369; 367/157, 159, 160, 161, 162

[56] References Cited

U.S. PATENT DOCUMENTS

| | | | |
|---|---|---|---|
| 3,182,284 | 5/1965 | Green | 310/369 |
| 3,474,403 | 10/1969 | Massa et al. | 310/369 |
| 4,072,871 | 2/1978 | Wilson | 310/333 |
| 4,633,119 | 12/1986 | Thompson | 310/325 |
| 4,972,390 | 11/1990 | Pagliarini, Jr. | 367/158 |
| 5,038,612 | 8/1991 | Thelen et al. | 73/493 |
| 5,109,698 | 5/1992 | Owen | 73/632 |
| 5,159,580 | 10/1992 | Andersen et al. | 367/132 |
| 5,798,599 | 8/1998 | Harwood | 310/323 |
| 5,861,704 | 1/1999 | Kitami et al. | 310/369 |

Primary Examiner—Richard A. Moller
Attorney, Agent, or Firm—L. E. Carnahan; Alan H. Thompson

[57] ABSTRACT

A wide bandwidth, ultrasonic transducer to generate nondispersive, extensional, pulsed acoustic pressure waves into concrete reinforced rods and tendons. The wave propagation distance is limited to double the length of the rod. The transducer acoustic impedance is matched to the rod impedance for maximum transfer of acoustic energy. The efficiency of the transducer is approximately 60 percent, depending upon the type of active elements used in the transducer. The transducer input energy is, for example, approximately 1 mJ. Ultrasonic reflections will occur at points along the rod where there are changes of one percent of a wavelength in the rod diameter. A reduction in the rod diameter will reflect a phase reversed echo, as compared with the reflection from an incremental increase in diameter. Echo signal processing of the stored waveform permits a reconstruction of those echoes into an image of the rod. The ultrasonic transducer has use in the acoustic inspection of long (40+foot) architectural reinforcements and structural supporting members, such as in bridges and dams.

18 Claims, 4 Drawing Sheets

HIGH ENERGY, LOW FREQUENCY, ULTRASONIC TRANSDUCER

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to ultrasonic inspection, more particularly to a wide bandwidth ultrasonic transducer, and more particularly to a high energy, low frequency, ultrasonic transducer for acoustic inspection of long members, such as steel reinforcement rods located in concrete.

The ultrasonic sandwich transducer was developed 75 years ago by Langevin. Conventional ultrasonic systems are designed for the inspection of relatively thin sections with relatively unrestricted lateral dimensions. These ultrasonic systems are designed to perform inspections on materials with ≧3:1 width to thickness aspect ratio. This aspect ratio is required to avoid problems in waveform definition, such as refraction, reflection, dispersion, and diffraction that may distort the waveform. There are materials that do not and can not conform to this aspect ratio, but must still be inspected, such as rods, columns, cables, and tendons. Cylindrical structural members are used to strengthen concrete, and these steel reinforcements are often located deeply within concrete or geological structures. In all installations, the diameter of the reinforcements is much smaller than the length; as an example, 1.375 inch diameter by 50 feet long.

Attenuation of sound is proportional to the frequency of the sound and to the distance of sound propagation, among other factors. High energy ultrasound has had application in soldering, welding, and cutting of various difficult materials, but these instruments gain their advantage by the use of a modified cone, acoustic transformer that must be lightly coupled to the work surface and are unsuitable, due to damping, for the hard coupled propagation of sound into materials, such as a rod. In addition, the horn type acoustic transformer is generally excited with a continuous wave, and an inspection transducer is generally excited with a pulsed wave for the interrogation of echoes from defects. Thus there has been a need in the art for an ultrasonic inspection system for long length rods, columns, cables, and tendons.

The present invention provides a solution to the above-mentioned need by providing a wide bandwidth, ultrasonic transducer to generate nondispersive, extensional, pulsed acoustic pressure waves into concrete reinforcement rods and tendons. Two major problems were solved by the ultrasonic inspection transducer for rods, these being: (1) the ultrasonic wavelength must be greater than five times the major diameter of the rod, and (2) the bandwidth must be equal to or greater than the central operating frequency of the transducer to produce echoes that retain polarity and definition relating to the changes in rod dimensions along the length of the rod. Thus the present invention provides a high energy, low frequency, ultrasonic transducer, wherein the transducer acoustic impedance is matched to the rod impedance for maximum transfer of acoustic energy, and ultrasonic reflections will occur at points along the rod where there are changes of one percent of a wavelength in the rod diameter.

SUMMARY OF THE INVENTION

It is an object of the present invention to provide an acoustic inspection system for long structural supporting members, such as rods and tendons.

A further object of the invention is to provide a sandwich ultrasonic transducer for testing the integrity of long members wherein only one end is exposed.

A further object of the invention is to provide a high energy, low frequency, ultrasonic transducer.

Another object of the invention is to provide a wide bandwidth, ultrasonic transducer to generate nondispersive, extensional, pulsed acoustic pressure waves into concrete reinforcement rods and tendons.

Another object of the invention is to provide an ultrasonic transducer for inspection of rods and tendons which have an acoustic impedance matched to the rod impedance for maximum transfer of acoustic energy.

Other objects and advantages of the present invention will become apparent from the following description and accompanying drawings. The present invention involves a sandwich ultrasonic transducer for use in inspection of long structural supporting components having only one end exposed. The low frequency ultrasonic transducer uses thin piezoelectric disks with a thin member between the adjacent piezoelectric disks, and the disks are centered between the masses of solids. When multiple elements are joined together, the elements are mechanically in series, but electrically in parallel. The total displacement caused by the pressure wave will be proportional to the summation of the number of elements. The transducer acoustic impedance is matched to the rod impedance for maximum transfer of acoustic energy, with the efficiency of the transducer being about 60 percent, depending upon the type of active elements used in the transducer. Ultrasonic reflections will occur at points along the rod where there are changes of one percent of a wavelength in the rod diameter, with a reduction in rod diameter being reflected as a phase reversed echo, as compared with the reflection from an incremental increase in diameter. Echo signal processing of the stored waveform permits a reconstruction of these echoes into an image of the rod.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Figure 2:
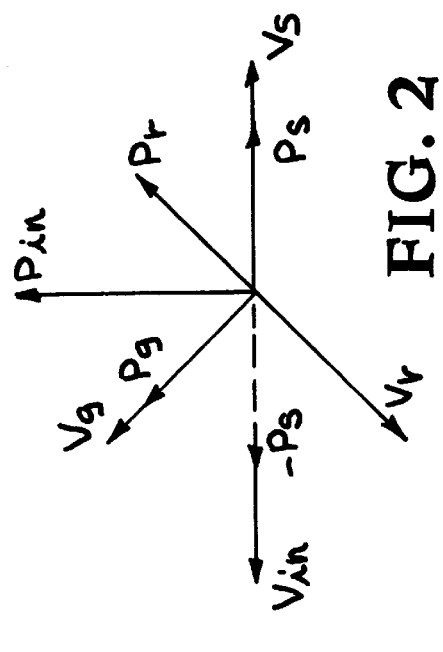
FIGS. 1–4 are vector diagrams showing the relationship of acoustic pressure and velocity.
Figure 4:
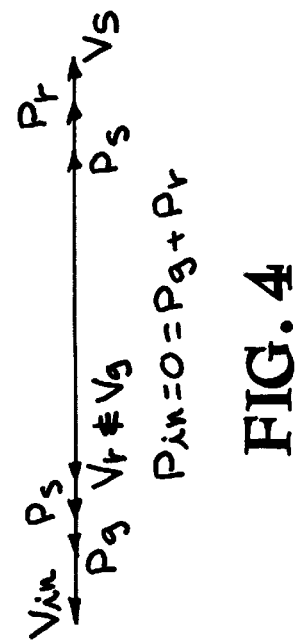
Figure 1:
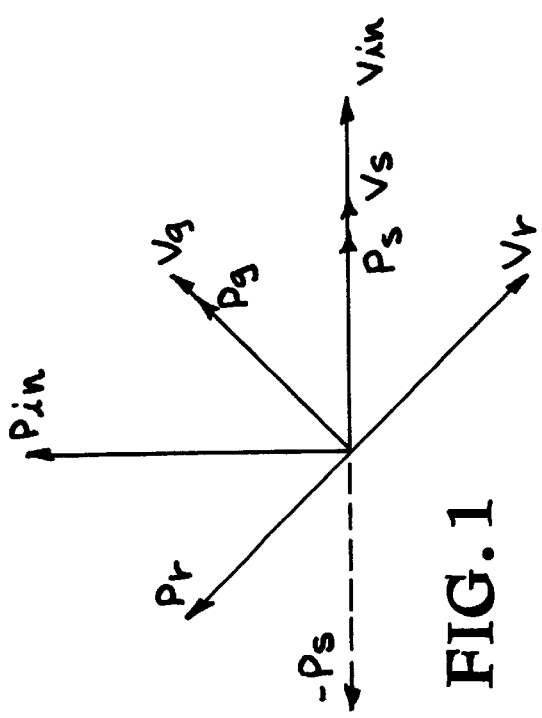
Figure 3:
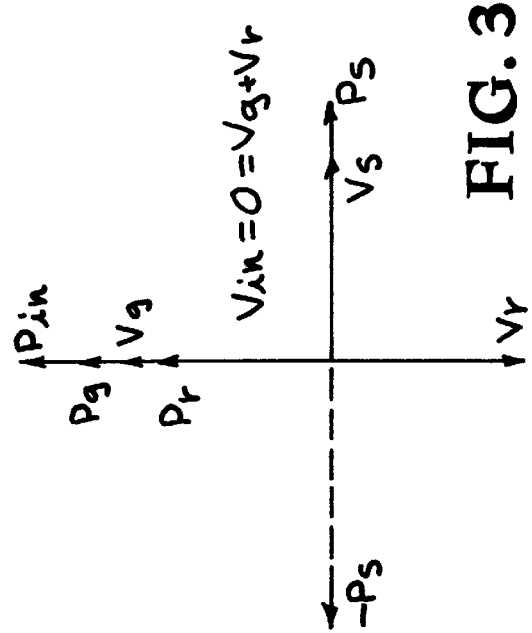

The invention is directed to a high energy, low frequency ultrasonic transducer. The transducer is of a sandwich-type having a number of piezoelectric disks centered between two end pieces or masses of solid material, and including a separator disk intermediate each pair of disks. The ultrasonic transducer is of a wide bandwidth capable of generating nondispersive, extensional, pulsed acoustic pressure waves into concrete reinforcement rods and tendons exposed only at one end.

As pointed out above, the ultrasonic transducer was developed over 75 years ago. Since then, various sandwich configurations have been developed. The sandwich construction has enabled the present invention which involves a low frequency transducer using thin piezoelectric disks that would otherwise respond only to very much higher frequencies. Like the prior high frequency piezoelectric disk, the high energy, low frequency piezoelectric disks of the present invention are centered between two solid end pieces or masses. A separator is located between the adjacent piezoelectric disks. The piezoelement, $L_O$, length is based upon a single thin element. When multiple elements are joined together, the elements are mechanically in series, but electrically in parallel. The total displacement caused by the pressure wave will be proportional to the summation of the number of elements. The solid ends could be either metal or plastic, depending upon the acoustic impedance matching required to the load, or device to be insonified. The back mass length is identified as $L_1$, and the front mass length as $L_2$. Each mass has an acoustic impedance defined by the product of its density, acoustic extensional velocity, and cross-sectional area. The length for each mass is determined by transmission line theory, originally developed for electrical circuits. The front mass, $L_2$, may approximate $\lambda/4$ long for the optimum power factor. However, for an end length <$n\lambda/4$, where "n" is an odd integer, the length becomes mass related, or inductive, and lowers the transducer frequency. If the end length >$n\lambda/4$, the length becomes stiffness related, or capacitive, and raises the resonant frequency of the transducer. In transmission line theory, the length of either $L_1$ or $L_2$ may be proportional to a $3\lambda/8$ shorted section (capacitive, stiffness), or a $\lambda/8$ shorted section (inductive, mass). The shorted section is the result of the air to solid interface, wherein the air impedance is nearly a short circuit when compared with the impedance of the solid. The impedance of a shorted $\lambda/8$ section is $Z_S=JZ_C$ Tan ($\theta$), and the impedance of a shorted $3\lambda/8$ section is $Z_S=JZ_C$ Cot ($\theta$). The relationship of acoustic pressure and velocity may be better understood by looking at the vector diagrams shown in FIG. 1 through FIG. 4. The designations shown on the vector diagrams are as follows: V is the phase velocity, P is the acoustic pressure. The subscripts indicate, g=generator end, s=shorted end, r=reflected wave front, and n=the resulting input to the acoustic line.

Figure 6:
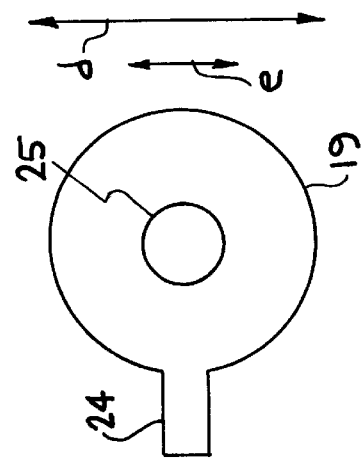
FIG. 6 is an enlarged view of the separator located intermediate the piezoelectric disks of FIG. 5.
Figure 5:
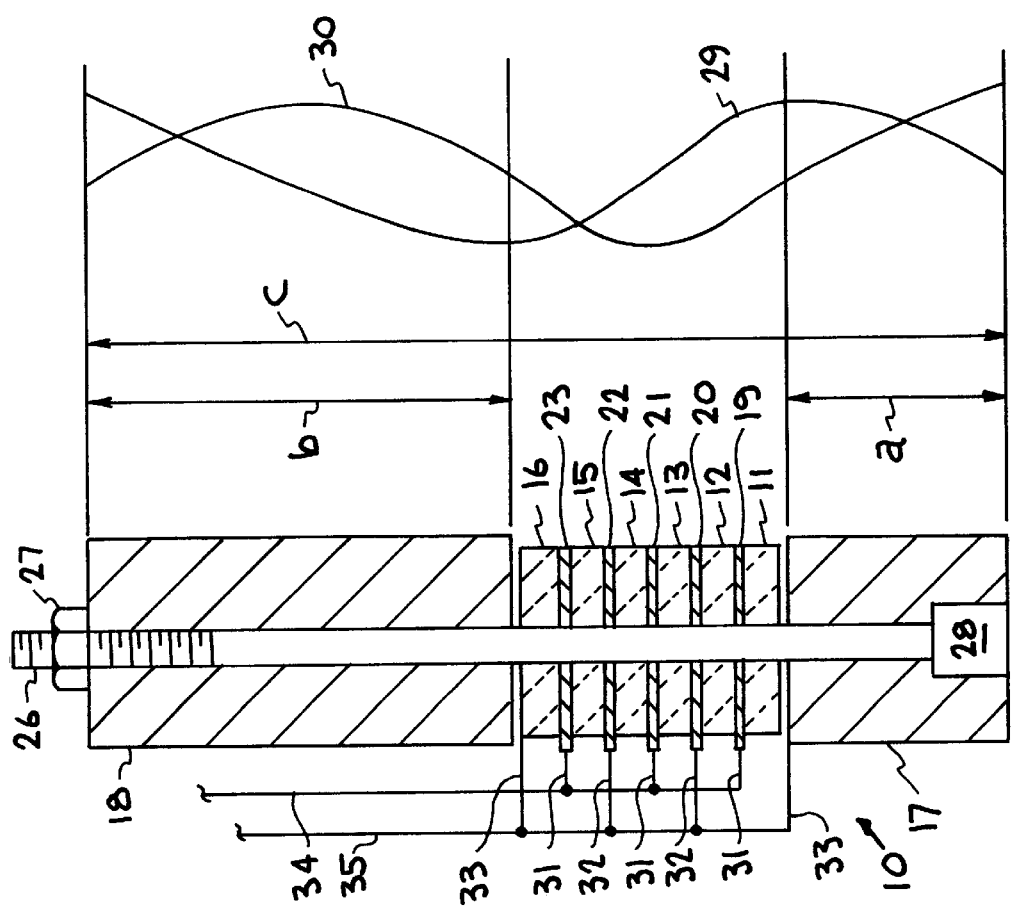
FIG. 5 is a partial cross-section of an embodiment of a sandwich ultrasonic transducer made in accordance with the present invention.

The front mass $L_2$ is generally close to a $\lambda/4$, and the back mass $L_1$ is generally close to a $\lambda/2$. The interface (or separator) between each piezoelectric element, shown in FIGS. 5 and 6, is a bronze fabric or member, 0.003 inch thick. A grease (Apiezon) is wiped onto the fabric to provide good acoustic coupling between the elements and from the elements to the end pieces. The end pieces should always be at ground potential. The bronze fabric permits the soldering of wires to make contact to the element electrodes. The wires are then sorted and bundled to electrically wire the elements in parallel, while keeping the elements mechanically in series. The overall displacement of the piezoelectric stack is equal to the displacement of single element multiplied by the number of elements. The thickness of the interspersed bronze fabric increases the length of the transducer and causes the transducer resonant frequency to be reduced. It is important that large excitation pulses cause the piezoelectric stack to compress rather than expand because the elements might otherwise fracture from the large displacements: Ceramics can withstand far more compression than tension. The loading bolt and nut are required to have a very high tensile strength, and the bolt is usually torqued to load the transducer piezoelectric elements to about 3,000 pounds per square inch (20.7 MPa) of compressive loading. For example, a 0.25 inch by 20 threads per inch, class 8, lubricated bolt and nut should be torqued to about 132 to 138 pound inches. When the front plate, $L_2$, is $\lambda/4$ long, Langevin showed that the governing formula is:

$$Z=(\rho_P C_P)^2/\rho_O C_O$$

where the subscripts P refer to the plate and O refers to the load. The electrical impedance into the transducer is:

$$R_E = \frac{1.2}{4\alpha^2} = Z_R$$

where $\alpha$ is the transformation factor. The impedance matching network is made from an additional $\lambda/4$ section of the front mass according to the formula:

$$Z_P = \sqrt{Z_E Z_L}$$

where E is the effective load impedance on the generator, P is the impedance of the transformer plate, and L is the impedance of the load.

The design formula for the transducer is a transcendental solution arrived at by the following equation:

$$\frac{\omega L_O}{V_O} + \tan^{-1}\left[\left(\frac{A_1 \rho_1 V_1}{A_O \rho_O V_O}\right)\tan\frac{\omega L_1}{V_1}\right] + \tan^{-1}\left[\left(\frac{A_2 \rho_2 V_2}{A_O \rho_O V_O}\right)\tan\frac{\omega L_2}{V_2}\right] = \pi \equiv 180°$$

where:

$L_1$, $L_2$, $L_O$ are the lengths of the back plate, front plate, and ceramic sections $V_1$, $V_2$, $V_O$ are the sound velocities in the above lengths $\rho_1$, $\rho_2$, $\rho_O$ are the densities for the above lengths $A_1$, $A_2$, $A_O$ are the cross sectional areas for the above lengths The output impedance of the transducer may need to be impedance matched to the load impedance. The load impedance is defined for a rod as: $Z\epsilon=\rho C\epsilon\pi D^2/4$. The $\lambda/4$ impedance matching transformer (see FIG. 8) must be the geometric mean of the input (transducer) and output (rod) terminations:

$$Z_T = \sqrt{Z_O Z_I} .$$

The output impedance of the transducer is the $\lambda/4$ inverted impedance of the transducer elements. The output impedance may be solved by using the formula for ZT, if the element impedance is known: $Z_T^2/ZI=ZO$. The diameter of the $\lambda/4$ matching transformer is:

$$D = \sqrt{4Z/\rho C_E \pi}$$

Acoustic echoes from the Howlett nut (see FIG. 8) may be expected to continue for a long period following the input pulse from the transducer. The multiple echoes are caused by a large difference in the acoustic impedance between the grip-nut and the tendon. Conservation of energy suggests that if much of the energy is used to generate echoes within the nut, little energy will remain to propagate down the length of the tendon. The appropriate action would be to prevent the acoustic impedance mismatch at the top of the tendon.

Figure 8:
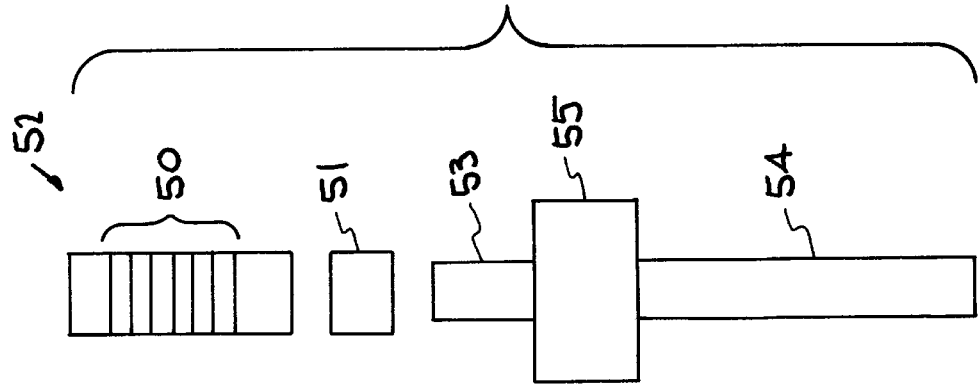
FIG. 8 is an exploded view of the transducer of FIGS. 5 or 7 in combination with components of a system for a tendon undergoing acoustic inspection.

The transducer output impedance must be matched to the load impedance. A relatively simple method to produce impedance matching is through a quarter wavelength transformer. A quarter wavelength stub will invert its termination, providing the termination is purely resistive. However, some tendons are not conducive to such simple impedance matching because the tendon assembly is composed of several complex impedances. That is, the tendon assembly consists of a short length of exposed tendon, followed by a fat, stubby jam (Howlett) nut, followed by the remaining length of tendon extending down to the bottom anchors, as shown in FIG. 8. Each element of the assembly may be described by a vector impedance: an impedance possessing both magnitude and direction. The top structure of the tendon assembly shown in FIG. 8 is capable of slight modification, such as extending the length of the exposed tendon by threading another rod to the end, or by adding a collar to the top face of the Howlett nut. Either modification will significantly change the impedance of the affected component. The design of a quarter wavelength transformer is restricted to matching pure resistive elements. The transformer cannot match conditions wherein there are (acoustic) mass and/or stiffness controlled elements on either side of the transformer. Mass and stiffness controlled elements are reactive and will cause a phase angle combined with an impedance magnitude. A correction to the impedance of the tendon assembly is most easily accomplished by slightly changing the length of a grip-nut (see FIG. 9). The technique for increasing the length of the grip-nut may be accomplished by adding a collar that is acoustically coupled to the grip-nut and the tendon end. The purpose behind the modification is to make the grip-nut appear to be one-half wavelength in height. A one-half wavelength section will repeat its termination. If the nut is forced to appear as a half-wavelength element, the nut will acoustically disappear from the acoustic response. The long duration ringing at the beginning of the acoustic record is thereby temporally reduced.

A plate that is terminated in a zero impedance (vacuum or air) and is thinner than $\lambda/4$, has an impedance that becomes mass-like (inductive) and lowers the resonance frequency of the system.

A plate that is terminated in a zero impedance and has a thickness between $\lambda/4$ and $\lambda/2$ becomes stiffness-like (capacitive) and raises the resonance frequency of the system. As shown in the vector diagrams of acoustic pressure and velocity in FIGS. 2 and 5, a plate that is $\lambda/4$ will invert its termination, and a plate that is $\lambda/2$ will repeat its termination.

A quarter wavelength plate transforms the resistive load impedance according to: $(\rho_P C_P)^2/\rho_O C_O$, where subscripts, P and O refer to the plate and load, respectively.

The electrical input impedance to the piezoelement is determined by the load acoustic impedance taken through the transformer-like action of 1: equivalent turns ratio.

The front plate should be $$(Z_o^2 = Z_{IN} Z_{OUT}),$$

thickness, and the piezoelement and back plate follows the relationship:

$$\left(\tan \frac{2\pi d_m}{\lambda_m}\right)\left(\tan \frac{2\pi d_b}{\lambda_b}\right) = \frac{\rho_m C_m}{\rho_b C_b} \quad \text{EQUATION A}$$

Where the subscripts, m and b, refer to the piezoelement and back plate, respectively, and d is the thickness of the layer.

The electric impedance of the transducer is defined as $Re = ZR/4\alpha^2$, where $\alpha = e_{ij} S/L$, and S is the piezoelement driving area. L is the piezoelement thickness. The piezo-stack is stiffness controlled with a motional impedance that has a large capacitive reactance. The value $e_{ij}$ is a piezoelement constant: This capacitive component of the piezoelement must be canceled by the inductive back plate to form a low frequency resonance.

The front plate transforms the low mechanical load impedance to a high impedance at the piezoelement interface, thereby permitting the transducer to be used in water, if so desired.

At the opposite face of the piezoelement, there is a reactance: $\rho_m C_m \tan [k_m d_m + \pi/2]$. This reactance is canceled by the back plate. The air interface on one side of the back plate results in an interface to the piezoelement of: $\rho_b C_b \tan [k_b d_b]$. For cancellation of reactances, the two expressions must be added and set to zero with the result in Equation A.

Referring now to the embodiment of the sandwich, high energy, low frequency, ultrasonic transducer illustrated in FIGS. 5–9, the transducer generally indicated at 10 comprises a plurality of piezoelectric elements or disks 11, 12, 13, 14, 15, and 16 positioned intermediate a pair of end pieces or masses 17 and 18, with separators or members indicated at 19, 20, 21, 22, and 23, located intermediate disks 11–12, 12–13, 13–14, 14–15, and 15–16. The disks, separators and end pieces may be annular, square, rectangular, cylindrical, etc. A layer of grease, such as Apiezon is used across the separators (19–23) and between the end pieces 17 and 18 and the adjacent elements or disks 11 and 16 to provide good acoustic coupling between the elements and from the elements or disks to the end pieces. The end pieces 17 and 18 are at ground potential. The separators or members 19–23, an embodiment shown in FIG. 6, may be composed of bronze, such as a bronze fabric having a 0.003 inch thickness. The bronze separators or members 19–23 include tabs 24 that permit the soldering of wires to make contact to the element electrodes or disks 11–16 and a central opening 25 for alignment. Each of the disks 11–16 and the end pieces 17–18, like the separators 19–23, include a central opening, as more clearly seen in FIG. 7, through a loading bolt 26, which extends from and is tightened by a nut 27. Note that the central openings differ in diameters. A stud 28 is located in an end of the central opening opposite nut 27. FIG. 5 also illustrates a velocity wave 29 and a pressure wave 30. Note that the velocity wave 29 curves at the interface of end member 17 and disk 11, and again at the interface of end member 18 and disk 16. Also, wires or electrical leads 31 and 32 extend from alternate separator tabs 24, and wires 33 extend from outer disks 11 and 16 for connection to common leads 34 and 35. By way of example, end piece 17 has a length indicated by arrow a of 1.466 inches, end piece 18 has a length indicated by arrow b of 2.817 inches, with the transducer 10 having an overall length indicated by the arrow c of 5.81 inches. Separators 19–23, as shown in FIG. 6, have, for example, a diameter indicated by arrow d of 1.26 inches, with central opening 25 having a diameter indicated by arrow e of 0.45 inches, with the tab 24 having a length of 0.125 inch and width of 0.125 inch.

Figure 7:
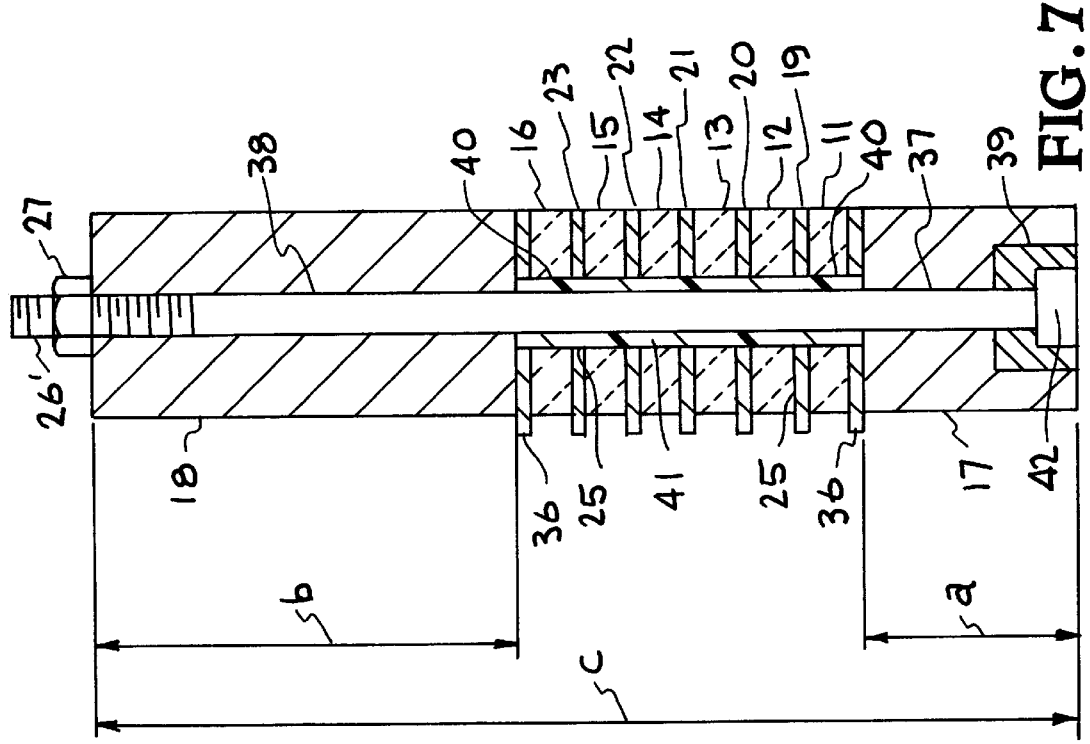
FIG. 7 is a partial cross-section of an embodiment generally similar to that of FIG. 5.

Referring now to FIG. 7, which is a partial cross-section of an embodiment similar to the FIG. 5 embodiment, and corresponding components are given similar reference numerals. In FIG. 7, two additional separators indicated at 36 are positioned between disks 11 and 16 and respective end pieces 17 and 18. End pieces 17 and 18 are provided with central openings 37 and 38 of the same diameter, such as 0.25 inches, with opening 37 including an enlarged diameter end section 39 in which stud 28 is located. Note that the diameter of openings 37 and 38 are smaller than openings 40 in disks 11–16 and openings 25 in separators 19–23. A sleeve 41 of polyethylene, for example, is located in openings 40 and 25 when bolt 26' is inserted through the openings 37, 40, 25 . . . 25, 40, and 38, with head 42 of bolt 26' being located in stud 28, and with the bolt 26' inserted through the components 17, 11, 19 . . . 23, 16 and 18, the nut 27 is tightened and torqued to load the piezoelectric disks or elements, for example, to about 3,000 pounds per square inch (20.7 MPa) of compressive loading.

By way of example, the end pieces 17 and 18 may have a diameter of 1.375 inches, with the openings 37 and 38 having a diameter of 0.25 inches; the bolt 26 being 0.25 inch diameter, 28 UNF, 6.5 inch length, Grade 8, 134 in. pound torque; the separators or bronze fabric members 19–23 and 36 being 0.003 inch thick rings, 1.3 inch OD, 0.465 inch ID; the piezoelectric disks or elements 11–16 being constructed of a ceramic material, such as lead-zirconate-titanate, EC-64, 1.257 inch OD, 0.45 inch ID, and 0.25 inch thick; the opening 39 may be 0.5 inch diameter, 20 UNF, 0.25 inch deep; and the stud 20 may be 0.5 inch diameter, 20 UNF, 0.5 inch length; with the outer diameter of the sleeve 41 being 0.45 inch.

As discussed above and illustrated in FIG. 8, a transducer 50, such as the transducer 10 of FIG. 5 or transducer 10' of FIG. 7 is shown in exploded view in combination with a tendon assembly composed of transformer 51, a tendon 52 having a stub section 53 and length section 54 tensioned by a Howlett nut 55. The transducer output impedance must be matched to the load impedance (tendon 52 and nut 55), and this is accomplished through the quarter wavelength transformer 51. Each element of the tendon assembly (components 53, 54, and 55) may be described by a vector impedance: an impedance possessing both magnitude and direction. As discussed above, the stub section 53 can be modified to change the impedance of the affected component. Also, since the exposed end of a tendon in a dam or other structure generally does not have a flat surface, it may be necessary to compensate for such, by flattening the end of the tendon and utilizing a collar to the grip-nut and compensating for such modification. If, as pointed out above, a grip-nut is used, the purpose behind the modification is to make the grip-nut appear to be one-half wavelength in height, and thus will acoustically diminish from the acoustic response.

Figure 9:
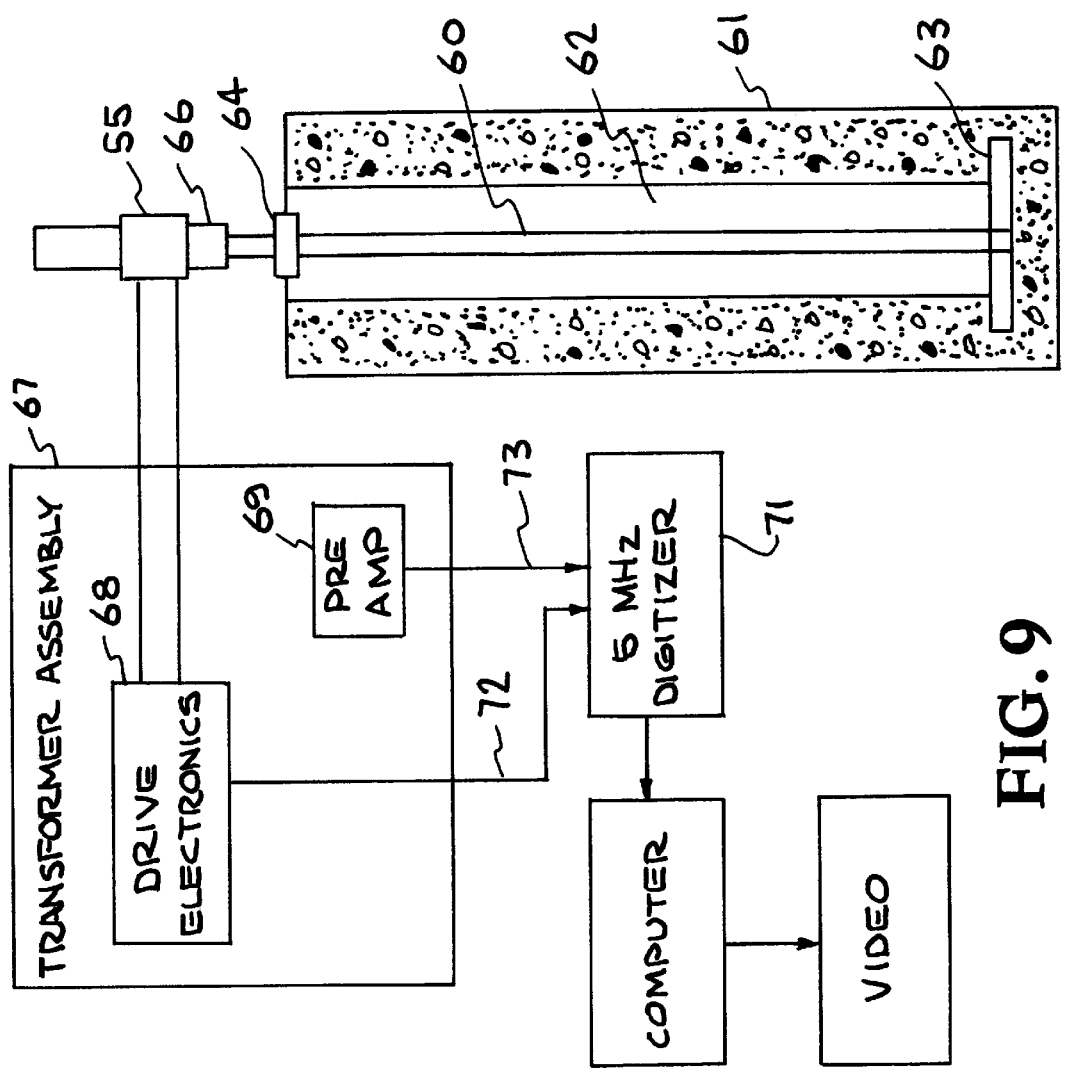
FIG. 9 illustrates an acoustic inspection system for a long tendon mounted in concrete of a dam and incorporating the transducer of FIGS. 5 or 7.

FIG. 9 illustrates an acoustic inspection system for a tendon mounted in the concrete spillway door of a dam. As shown, a tendon 60 (40'×1.375') is located in a concrete spillway door 61 via group backfill 62 and secured at the lower end to a tendon anchor plate 63. As in FIG. 8, the tendon includes a gripper socket nut (Howlett nut) 64 and is connected to a sandwich ultrasonic transducer 55 by a mounting stud 66. The piezoelectric elements or disks of the transducer 65 are connected to a transformer assembly 67 containing a drive electronics section 68 and a pre-amp section 69. A computer system generally indicated at 70 is connected to the drive electronics section 68 and to a 1 MHz digitizer 71, which is connected to the drive electrons section 68 via a trigger signal 72 and to the pre-amp section 69 via a signal 73. Ultrasonic reflections will occur at points along the tendon 60 where there are changes greater than one percent of wavelength in the tendon diameter. A reduction in the tendon diameter will reflect a phase reversed echo, as compared with the reflection from an incremental increase in diameter. Echo signal processing of the stored waveform permits a reconstruction of those echoes into an image of the tendon.

As pointed out above, the efficiency of the transducer is about 60 percent, depending upon the type of active elements or disks used therein. The transformer input energy is approximately 1 mJ. The wave propagation distance is limited to double the length of the tendon or rod. The transducer acoustic impedance is matched to the tendon or rod impedance for maximum transfer of acoustic energy. Thus it has been shown that the present invention provides a wide bandwidth (high energy, low frequency) ultrasonic transducer to generate nondispersive, extensional, pulsed acoustic pressure waves into concrete reinforcement rods or tendons.

While specific embodiments of the transducer have been illustrated and described, along with materials, parameters, etc., such are not intended to be limiting. Modifications and changes may become apparent to those skilled in the art, and it is intended that the invention be limited only by the scope of the appended claims.

The invention claimed is:

1. An ultrasonic transducer for inspecting an elongated member having an exposed end, comprising:

a plurality of axially aligned piezoelectric elements, a plurality of separators positioned adjacent said piezoelectric elements, each of said plurality of separators including a tab section for electrical connection, a pair of end pieces located at opposite ends of said axially aligned piezoelectric elements, a layer of grease intermediate each of said end pieces, piezoelectric elements, and separators, and means extending through said end pieces, piezoelectric elements, and separators for securing same together and to load the piezoelectric elements, wherein the transducer is adapted to be connected to the exposed end of the elongated member.

2. The ultrasonic transducer of claim 1, wherein said plurality of said piezoelectric elements, said plurality of separators, and said pair of end pieces are of an annular configuration, and each include a central opening extending therethrough.

3. The ultrasonic transducer of claim 1, wherein said plurality of separators are constructed of a bronze fabric.

4. The ultrasonic transducer of claim 1, wherein said plurality of piezoelectric elements include a ceramic material.

5. The ultrasonic transducer of claim 1, wherein said means extending through said end pieces, piezoelvectric elements and separators comprise a threaded bolt constructed to withstand a tension or tensile load of about 3,000 pounds per square inch.

6. The ultrasonic transducer of claim 5, wherein said bolt is provided with a sleeve adapted to be located only within said piezoelectric elements and said separators.

7. The ultrasonic transducer of claim 5, additionally including a stud located in an end of one of said end pieces and adjacent an end of said bolt.

8. The ultrasonic transducer of claim 1, in combination with a transformer and with an elongated member, said elongated member to be acoustically inspected.

9. The combination of claim 8, additionally including means for recording and processing echo signals produced by ultrasonic reflections of said elongated member upon acoustic pressure waves from said transducer being directed into said elongated member.

10. In an ultrasonic inspection system, the improvement comprising means for enabling ultrasonic inspection of an elongated member having only one exposed end, said improvement comprising:

a wide bandwidth ultrasonic transducer adapted to be connected to said exposed end of said elongated member;

said ultrasonic transducer being of a sandwich configuration, including a plurality of axially aligned piezoelectric elements having separators there-between.

11. The improvement of claim 10, wherein said ultrasonic transducer additionally includes a pair of end pieces and a threaded member for retaining said end pieces, piezoelectric elements, and separators, and for applying a torque to said piezoelectric elements.

12. The improvement of claim 11, wherein said piezoelectric elements are of a disk configuration having a central opening, wherein said separators are of an annular configuration having a central opening therein, wherein said end pieces are of a cylindrical configuration having a central opening therein, and wherein said threaded member extends through said central openings.

13. The improvement of claim 12, wherein said central openings in said piezoelectric elements and said separators are of a diameter larger than a diameter of said central openings in said end pieces, and additionally include an insulating sleeve about a section of said threaded member and located in said central openings of said piezoelectric elements and said separators.

14. The improvement of claim 13, wherein said central opening in one of said end pieces included a larger diameter end section, and additionally including a stud positioned in said larger diameter end section.

15. The improvement of claim 14, wherein each of said separators is provided with an outwardly protruding tab for electric connection thereto.

16. The improvement of claim 15, wherein said piezoelectric elements include a ceramic material, and wherein said separators comprise a member composed of bronze fabric.

17. The improvement of claim 11, additionally including a layer of grease intermediate adjacent piezoelement elements, separators, and end pieces to provide acoustic coupling there-between.

18. The improvement of claim 10, wherein said piezoelectric elements are mechanically in series and electrically in parallel.

* * * * *